US012560601B2

(12) United States Patent　　　(10) Patent No.:　US 12,560,601 B2

Fischl et al.　　　(45) Date of Patent:　Feb. 24, 2026

---

(54) DIRECT SAMPLE COLLECTION PAD AND METHOD OF USE FOR ASSAY DIAGNOSIS

(71) Applicant: ORASURE TECHNOLOGIES, INC., Bethlehem, PA (US)

(72) Inventors: Mark Fischl, Bethlehem, PA (US); Mark Emrick, Bethlehem, PA (US); Keith Kardos, Bethlehem, PA (US)

(73) Assignee: ORASURE TECHNOLOGIES, INC., Bethlehem, PA (US)

( * ) Notice: Subject to any disclaimer, the term of this patent is extended or adjusted under 35 U.S.C. 154(b) by 955 days.

(21) Appl. No.: 17/709,620

(22) Filed: Mar. 31, 2022

(65) Prior Publication Data

US 2022/0341927 A1　　Oct. 27, 2022

Related U.S. Application Data

(60) Provisional application No. 63/179,768, filed on Apr. 26, 2021.

(51) Int. Cl.
| | |
|---|---|
| *G01N 33/543* | (2006.01) |
| *B01L 3/00* | (2006.01) |
| *G01N 33/58* | (2006.01) |

(52) U.S. Cl.
CPC ...... *G01N 33/54388* (2021.08); *B01L 3/5023* (2013.01); *G01N 33/58* (2013.01); *B01L 2200/16* (2013.01); *B01L 2300/069* (2013.01); *B01L 2300/0825* (2013.01); *B01L 2300/123* (2013.01); *B01L 2400/0406* (2013.01)

(58) Field of Classification Search
None
See application file for complete search history.

(56) References Cited

U.S. PATENT DOCUMENTS

| | | | | |
|---|---|---|---|---|
| 4,441,509 A | * | 4/1984 | Kotsifas et al. | ... A61B 10/0291 |
| | | | | 600/570 |
| 6,303,081 B1 | | 10/2001 | Mink et al. | |
| 6,365,417 B1 | * | 4/2002 | Fleming | ........... G01N 33/54388 |
| | | | | 435/7.1 |
| 6,875,185 B2 | | 4/2005 | Wong | |
| 7,192,555 B2 | | 3/2007 | Mink et al. | |
| 7,488,298 B2 | * | 2/2009 | Patel | .................. A61B 5/14532 |
| | | | | 600/583 |

(Continued)

FOREIGN PATENT DOCUMENTS

| | | |
|---|---|---|
| AU | 2021200628 A1 | 3/2021 |
| CA | 3116909 A1 | 4/2020 |
| EP | 3225995 B1 | 5/2019 |

OTHER PUBLICATIONS

ORAQUICK. "OraQuick Advance HIV 1/2 Training Video" . . . Retrieved From The Internet: www.youtube.com/watch?v=I-GaHFUTYAO> Jun. 6, 2011; Entire Document.

*Primary Examiner* — Maris R Kessel
*Assistant Examiner* — Madison Taylor Herbert
(74) *Attorney, Agent, or Firm* — RAPHAEL BELLUM PLLC

(57) ABSTRACT

The invention relates to a direct sample collection pad for assay diagnosis of a sample without introducing an additional sampling device into the assay method. This simplifies the system and method of sample collection and assay diagnosis, thus reducing waste and potential for patient irritation or injury during diagnosis.

18 Claims, 14 Drawing Sheets

(56)              References Cited

U.S. PATENT DOCUMENTS

| | | |
|---|---|---|
| 2010/0239458 A1 | 9/2010 | Mink et al. |
| 2014/0363353 A1* | 12/2014 | Salvo ..................... G01N 21/78 |
| | | 422/417 |
| 2016/0167042 A1 | 6/2016 | Tyrrell |
| 2020/0116598 A1* | 4/2020 | Ling ..................... B01L 3/5023 |
| 2020/0241020 A1* | 7/2020 | Oshinski ................... B01L 3/52 |
| 2020/0371100 A1 | 11/2020 | Yearwood et al. |

\* cited by examiner

100

101

T1

103a

105

103b

1001

1003

107

DIRECT SAMPLE COLLECTION PAD AND METHOD OF USE FOR ASSAY DIAGNOSIS

CROSS-REFERENCE TO RELATED APPLICATION

This application claims benefit of priority from U.S. Provisional Application No. 63/179,768 filed on Apr. 26, 2021, the entire contents of which are incorporated by reference.

TECHNICAL FIELD

This invention relates to a sampling device that can also be used as a direct collection pad of an assay assembly for use with a developer solution vial. The direct sample collection pad incorporates two components into the assay assembly by combining the sampling device and collection pad in one unit. By providing a direct sample collection pad as part of an assay assembly, the use of a separate collection device is removed, thus reducing inefficiencies.

BACKGROUND

Diseases have resulted in pandemics and outbreaks throughout time. Accurate and fast diagnosis of the causative viral or bacterial pathogen is important to select the appropriate treatment, save people's lives, stop the epidemics, and reduce unnecessary use of drugs (e.g., antibiotics) in control and management of outbreaks. Point-of-care assays for detection of respiratory and other diseases include diagnostics devices based on assay devices including lateral flow assay (LFA) formats, which typically employ antibodies with visual detection of the endpoint immune complex formation and the use of recognition molecules, including nanoparticle labels or aptamers. See, e.g., U.S. Pat. Nos. 7,192,555 and 6,303,081. This results in an accurate and rapid test.

LFA devices often comprise a collection pad and an assay strip. The assay strip often includes a series of components, including a blocker pad, a conjugate pad, a nitrocellulose membrane, and an absorbent pad. The assay process is performed by wetting and transport of reagents as they interact with a liquid sample moving across the assay strip via a chromatographic lateral flow. A collected sample may be eluted from a sampling device into a developer solution, which is then removed. The assay device, which includes a collection pad, performs the assay process with the vial of sample that includes developer solution. The assay is performed as the liquid sample moves through the collection pad to an assay strip passing from the blocker pad to the conjugate pad to the nitrocellulose membrane and finally to the absorbent pad. Patent applications describing the use of such typical assay devices include U.S. Pat. App. Pub. Nos. 2020/0371100 and 2010/0239458.

Typical collection pads for LFA devices may include a rigid capillary matrix that can collect a sample with minimal manipulation (e.g., compression). These collection pads promote transmittance of a sample eluted from a sampling device rather than from direct collection of a sample because the collection pads are fairly rigid and, if used for direct collection, would cause discomfort and or injury to a patient during collection.

By wicking into an assay device, a developer solution facilitates elution of a sample from a sampling device (e.g., a swab) and transport of the sample with the developer solution. The same patent applications above, in particular, U.S. Pat. App. Pub. No. 2020/0371100, discusses the use of such developer solutions. One such developer solution includes an aqueous solution of surfactants, salts, preservatives, buffering agents, and other materials as known in the art. Buffer agents may include phosphate, Tris-Cl borate, bicarbonate, etc. Surfactants may include Tween 20, Triton X-100 or other non-ionic detergents. Preservatives may include anti-microbial and anti-fungal substances such as sodium azide.

In a conventional LFA device, a liquid sample moves from the collection pad to a blocker pad, where assay reagents on the blocker pad are hydrated. These reagents may contain animal proteins, salts, buffers, and detergents commonly used in the diagnostic industry for inhibiting non-specific reactions (blocking) and facilitating flow. A conjugate pad stores assay reagents, such as labels and antibodies, and a signal-generating reagent, which react with a target analyte in the sample, binding to the target, as the liquid sample continues through the assay device. As the liquid sample continues along the device, binding reagents in the nitrocellulose membrane capture the target analyte at a test line and provide a visual color line indicating the presence of the target analyte. The liquid sample continues to flow along the nitrocellulose membrane to the absorbent pad. The absorbent pad serves as the end reservoir for the liquid and wicks excess liquid. After a specified amount of time (e.g., about 1 to 10 minutes), a healthcare worker or test administrator or the individual self-tester will interpret the results.

To date, using conventional systems results in increased waste from requiring the use of both a collection pad and sampling device, will result in patient irritation due to additional steps and in instances where collection pads are used to collect samples pain or injury, and requires larger sample sizes for diagnosis. In particular, point-of-care systems for the diagnosis of respiratory diseases have been especially problematic.

SUMMARY OF THE INVENTION

The invention includes a direct sample collection pad and methods for use with assay assemblies. Systems and methods in accordance with the invention are used to diagnose diseases using a developer vial with developer solution, such as those used with an LFA. The LFA can be combined with the direct sample collection pad to reduce diagnostic steps, reduce waste, and maximize efficient use of a reduced sample size. The direct sample collection pads in accordance with the invention provide an accurate, sensitive, and rapid test with less waste and by reducing sample dilution.

The invention further relates to a direct sample collection pad for use with an LFA to minimize the use of buffer solution and to increase sample collection pad contact in the buffer solution. The direct sample collection pads include truncated and narrowed collection pads with slits.

The invention further relates to methods of using the direct sample collection pad in diagnosing respiratory diseases.

DETAILED DESCRIPTION OF THE INVENTION

The invention provides direct sample collecting pads and methods for use with an assay assembly. The pads and methods simplify diagnosis of respiratory diseases, including a number of viruses (approximately 80% of all respiratory diseases being viral) such as influenza A and B viruses, parainfluenza virus (PIV) type 1 (PIV1), PIV2, PIV3, respiratory syncytial virus (RSV), adenovirus, rhinovirus, avian influenza viruses (H5N1, H7N7, and H7N3), human metapneumovirus (hMPV), severe acute respiratory syndrome (SARS), coronavirus (COVID-19), bocavirus, enterovirus, PIV4, parvovirus types 4 and 5, and mimivirus, all of which affect the respiratory tract. Although discussed below in exemplary embodiments of the invention that may refer specifically to COVID-19, the invention may be used for any number of sampling collection methods for disease diagnosis, including, for example, sample collection by swabbing from surfaces or from a patient's bodily fluid. Although the description of the invention may refer specifically to nasal sample collection, the collection of samples may include saliva sampling, other sampling of bodily fluids, or sampling from surfaces. The invention may generally be used in a point-of-care sample collecting and rapid testing method via low-volume fluid flow assay testing.

COVID-19 Lateral Flow Assays

Immunoassays are being employed on the frontlines to determine whether a person has COVID-19 or has been exposed to it. Positive results from an immunoassay can indicate the presence of SARS-1 and SARS-2 Nucleocapsid Antigen. Clinical correlation with patient history and other diagnostic information is necessary to determine patient infection status. Positive results are presumptive and require additional testing to confirm the presence of SARS-CoV-2 antigens that cause COVID-19 disease. Positive results do not rule out bacterial infection or co-infection with other viruses. Negative results do not preclude SARS-CoV-2 infection and are not used as the sole basis for patient management decisions. Negative results are combined with clinical observations, patient history, and epidemiological information.

A developer solution vial of the invention may be used with a LFA device to test for COVID-19. Such an LFA device typically has a collection pad used in a COVID-19 rapid antigen tests as an in vitro diagnostic single-use immunoassay for qualitative detection of SARS-1 and SARS-2 Nucleocapsid Antigen in nasal samples collected from the anterior nares in individuals who meet the COVID-19 clinical and/or epidemiological criteria.

Direct Sample Collection Pad

Figure 1:
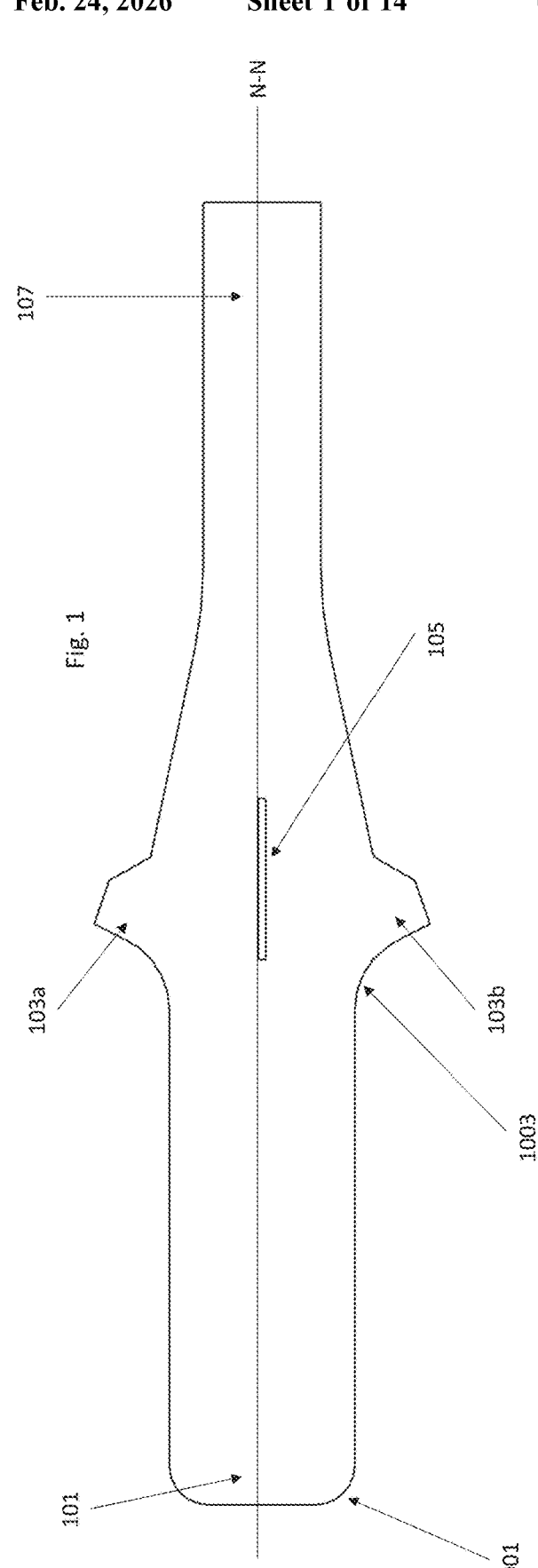
FIG. 1 is an exemplary front view of a direct sample collection pad without slits for use in an assay assembly in accordance with one embodiment of the invention.
Figure 2:
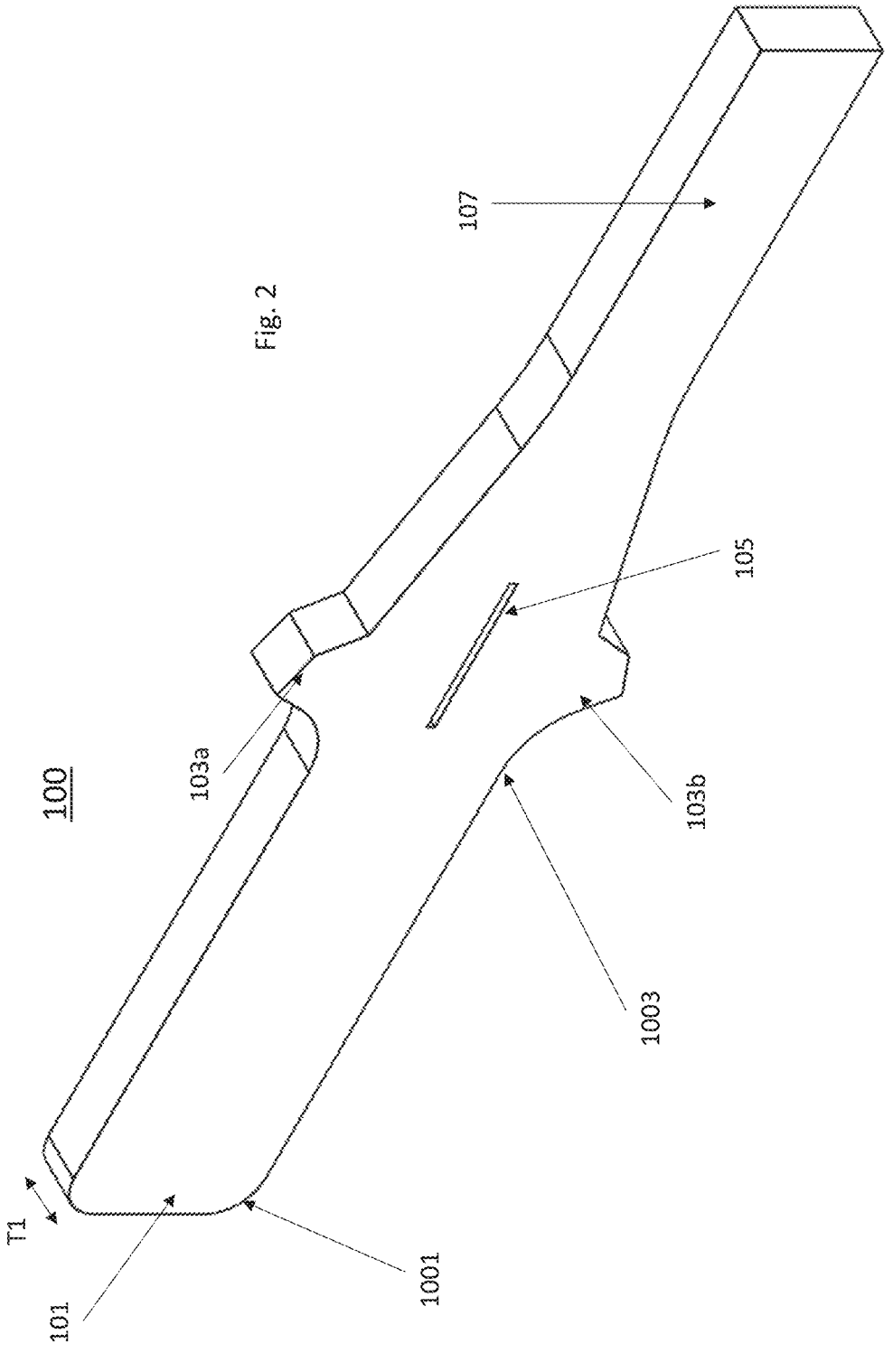
FIG. 2 is an exemplary front perspective view of the direct sample collection pad without slits for use in an assay assembly in accordance with one embodiment of the invention.

FIGS. 1 and 2 show exemplary front view and front perspective view illustrations, respectively, of a direct sample collection pad 100 without slits for use in an assay assembly, of the invention. The direct sample collection pad 100 is used in conjunction with an assay, such as an LFA, for use in diagnostics testing for a disease. In the exemplary embodiment, the direct sample collection pad 100 is part of an assay assembly including the housing 501 (shown in FIG. 5), assay assembly 500 (shown in FIG. 5), and collection pad 100. The collection pad 100 is placed in a housing 501 with the LFA. The collection pad 100 and LFA are interfaced together to direct collected sample through the assay assembly for a final presentation of an indication of positive or negative test results. In some embodiments, the direct sample collection pad 100 is made of the same material as a collection pad described above.

The direct sample collection pad 100 includes a sampling portion 101, seated wing portions 103a and 103b, housing security portion 105, and interface portion 107. The sampling portion 101 is placed in direct contact with a patient or surface for collecting samples. For example, the direct sample collection pad 100 is placed in contact with a patient's respiratory tract, saliva, or other bodily fluids for sample collection. The sampling portion 101 collects a sample from the patient and is then placed in a vial of developer or buffer solution to run the test. The sampling portion 101 is generally the only part of the assay assembly that touches the developer or buffer solution in the vial. The developer or buffer solution is drawn into the body of the direct sample collection pad 100 and through to the rest of the assay assembly. The sampling portion 101 can include an elongated rectangular shape (see FIG. 1 along line N-N) to provide a long and wide sampling surface. The sampling portion 101 can also include a thickness T1, as shown in FIG. 2, for stiffness when the direct sample collection pad 100 is made from a nitrocellulose material. The stiffness provides a rigidity to the direct sample collection pad 100 itself to provide a push-back when the sampling portion 101 is scraped along a surface. This rigidity limits the sampling portion 101 from bending too much during sampling. For example, if the direct sample collection pad 100 is not stiff enough, very little to no scraping along the surface would occur by the pad. Due to the nitrocellulose material, which provides a dense structure along the longitudinal axis N-N, during collection a sampling portion 101 that is too thin may be too flexible to press against a collection surface. In some embodiments, the edges and/or corners of the sampling portion 101 are rounded to provide a smoother surface that is less perceptible when collecting a sample from a patient.

In some embodiments, the sampling portion 101 may include other various shapes that conform with the shape and size of a cavity of a developer solution vial. This serves to reduce void volume of the vial when the collection pad 100 is placed in the vial. The sampling portion 101 is designed and manufactured to collect a large enough sample to accurately run the assay diagnosis. For example, a sampling portion 101 for collection from the tongue may be (relatively?) wider than shown in FIG. 1 to press against a wider surface of the tongue during collection, as long as the developer solution vial has a wider cavity as well.

The seated wing portion 103a and 103b have a rounded smooth edge 1003 near the sampling portion 101. The surface of the rounded smooth edge 1003 provides a resting surface along the thickness of the direct sample collection pad 100 to contain an interior surface of the housing 501 (shown in FIG. 5) of the assay assembly and/or to conform to a surface of the vial to rest the assay assembly in the vial without touching the furthest surface of the sampling portion 101 to the bottom of the vial. This prevents compression of the nitrocellulose material within the vial and draws the buffer or developer solution evenly through the direct sample collection pad 100. In some embodiments, the seated wing portion 103a and 103b may extend beyond the outer edge of a vial to stably rest the assay assembly on the vial. The thickness T1 may also provide additional surface area for the seated wing portion 103a and 103b to rest on the vial.

The housing security portion 105 interfaces with the housing 501 (shown in FIG. 5) of the assay assembly 500 (shown in FIG. 5) to retain the direct sample collection pad 100 and to prevent excess movement of the direct sample collection pad 100 within the housing 501 of the assay assembly. In one exemplary embodiment shown in FIGS. 1 and 2, the housing security portion 105 is an opening held in place with a corresponding protrusion inside the hollow section 5001 of the housing 501 (shown in FIG. 8) of the assay assembly 500 (shown in FIG. 5). As shown in FIG. 1, the housing security portion 105 is a narrow-elongated opening. The housing security portion 105 extends longitudinally to the housing of the assay assembly and to the corresponding protrusion to prevent rotation and other movement of the direct sample collection pad 100. In some exemplary embodiments, the housing security portion 105 can include one or more openings for corresponding protrusions inside the hollow section 5001 of the housing 501 of the assay assembly 500. The one or more corresponding protrusions retain the direct sample collection pad 100 and minimize movement within the housing of the assay assembly. Although the seated wing portion 103a and 103b and housing security portion 105 are symmetrically positioned around the same location of the longitudinal axis N-N in the embodiment shown in FIG. 1, in other embodiments, the seated wing portion 103a and 103b can be placed at different locations with respect to the housing security portion 105. The location of the seated wing portion 103a and 103b may be based on the seating surfaces of differently shaped vials.

The interface portion 107 contacts a blocker pad surface of the assay assembly (not shown separately) thus providing an interface between the direct sample collection pad 100 and the assay assembly. The interface portion 107 allows the developer or buffer solution to draw samples from the sampling portion 101 through the direct sample collection pad 100 to the blocker pad and through the rest of the assay assembly for testing.

The vial and/or assay assembly housing can include a portion for interfacing with the direct sample collection pad 100. This interface can correspond to a seating portions 103a and 103b for the direct sample collection pad 100 to rest upon while the assay works. The seating portion 103a and 103b prevents compression of the sampling portion 101 of the collection pad 100 when placed in a vial. Once seated, the sample is wicked through the direct sample collection pad 100 and directed to the interface portion 107 which contacts the assay strip beginning with the blocker pad. The seating portions 103a and 103b are extensions between the interface portion 107 and the sampling portion 101. These extensions are generally rounded to contour to a seating surface of the vial or, in some embodiments, may expand beyond the edge of the vial to securely rest upon the assay assembly.

The direct sample collection pad 100 length along axis N-N axis of FIG. 1 is about 42.16 mm; the thickness T1 is about 1.57 mm; the housing security portion 105 length is about 5.207 mm±0.13 mm and about 0.25 mm width; the seated wing portions 103a and 103b extend from the sampling portion 101 width of about 6 mm to around a width of about 10.83 mm (extend out from the sampling portion 101 width of about 2.415 mm on each side; the interface portion 107 width is about 3.810 mm±0.13 mm; and the sampling portion 101 length is about 16.03 mm.

Figure 3:
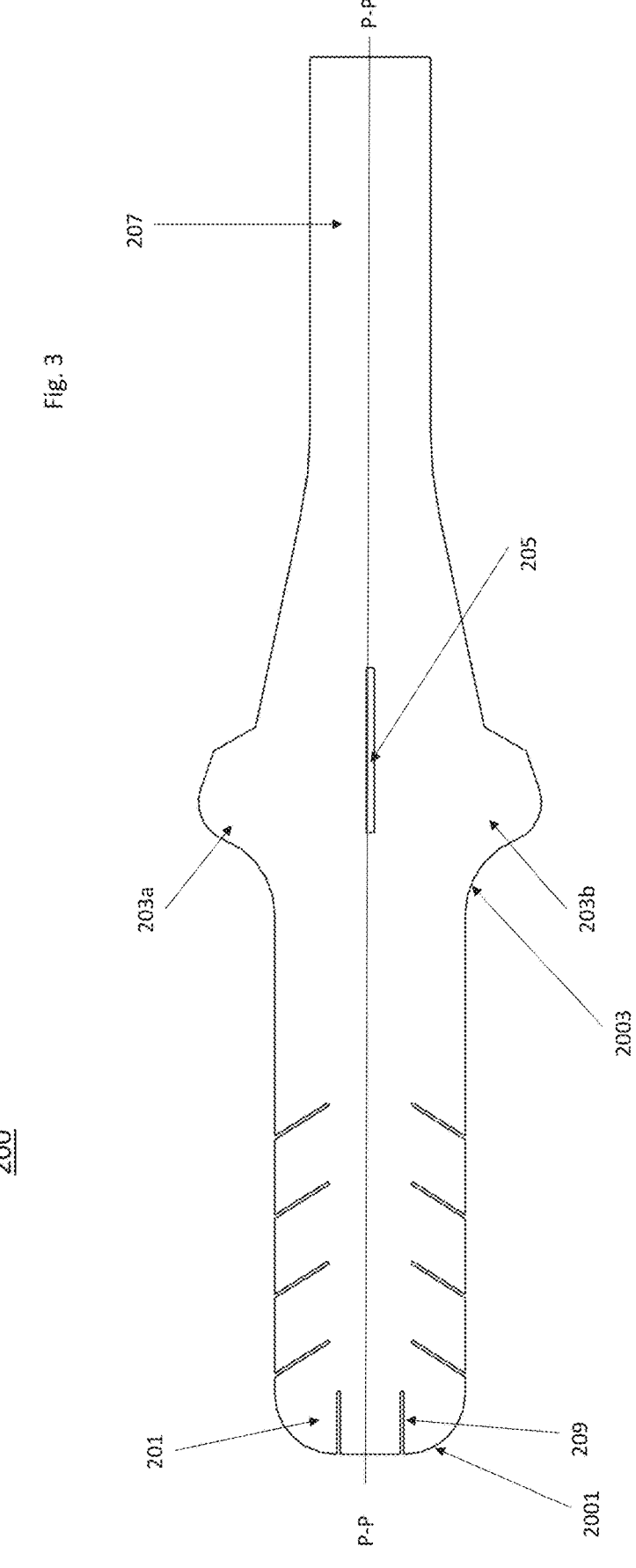
FIG. 3 is an exemplary front view of a direct sample collection pad with slits for use in an assay assembly in accordance with one embodiment of the invention.
Figure 4:
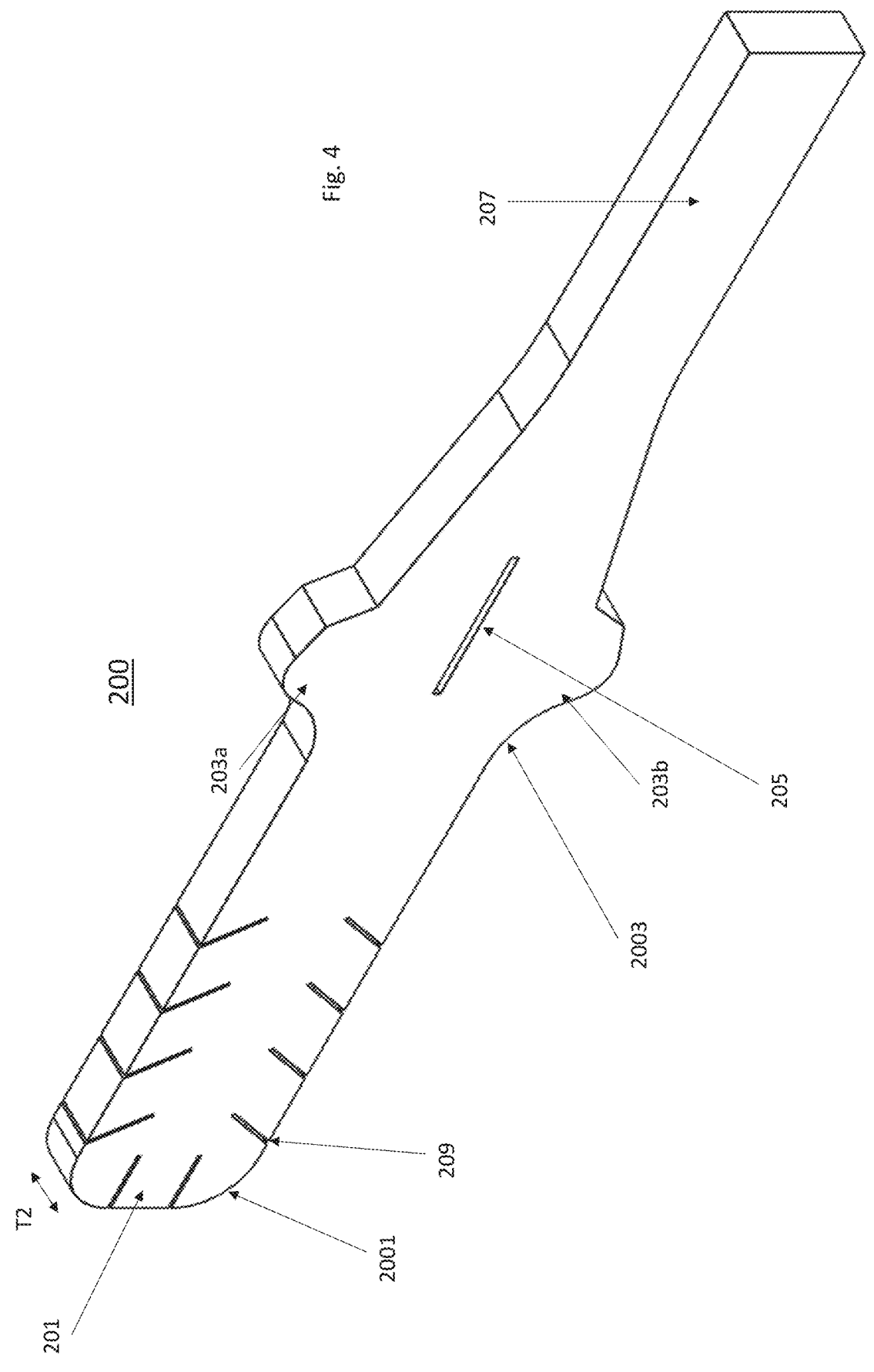
FIG. 4 is an exemplary front perspective view of the direct sample collection pad with slits for use in an assay assembly in accordance with one embodiment of the invention.

FIGS. 3 and 4 show exemplary front and front perspective view illustrations, respectively, of a direct sample collection pad 200 with slits 209 for use in an assay assembly in accordance with the invention. Similar to the direct sample collection pad 100 of FIGS. 1 and 2, the direct sample collection pad 200 is used in conjunction with an assay, such as an LFA, for use in diagnostics testing for a disease. The collection pad 200 is placed in a housing with the LFA. The collection pad 200 and LFA are interfaced together to direct a collected sample through the assay assembly for a final visual indication of positive or negative test results. The direct sample collection pad 200 and the direct sample collection pad 100 (shown in FIGS. 1 and 2) are mostly the same except for slits 209 in the sampling portion 201 of the direct sample collection pad 200.

The direct sample collection pad 200 includes a sampling portion 201, seated wing portions 203a and 203b, housing security portion 205, interface portion 207, and slits 209. The portions of direct sample collection pad 200 are largely equivalent to the respective portions of the direct sample collection pad 100. The key difference between the pads 100 and 200 is the slits 209. The slits 209 provide a feathering for the direct sample collection pad 200. The slits 209 provide flexibility, while retaining stability, of the direct sample collection pad 200 and increase comfort for patients when collecting samples from anatomical surfaces, such as from a nasal cavity or a tongue. The slits 209 can be evenly spaced along at least one edge of the direct sample collection pad 200. The slits 209 can be cut directionally toward an opposite end of the direct sample collection pad 200. For example, as shown in FIG. 3, the slits 209 are cut toward the interface portion 207 of the direct sample collection pad 200. In the direct sample collection pad 200 shown, the slits 209 along the sides of the sampling portion 201 are cut at around a 45-degree angle from axis P-P toward the interface portion 207. In some embodiments, the slits 209 are cut between 10 and 80 degrees from axis P-P. The slits 209 at the end opposite the interface portion 207 are cut parallel to axis P-P.

In some embodiments, even the slits 209 at the end opposite the interface portion 207 are cut at a slight angle between 0 and 45 degrees.

The length of direct sample collection pad 200 along axis P-P is about 42.16 mm. The thickness T2 is around 1.45 mm. The housing security portion 205 length is around 5.21 mm±0.13 mm and around 0.25 mm width. The seated wing portions 203a and 203b extend from the sampling portion 201 width of around 6 mm to around a width of around 10.68 mm. The seated wing portion 203a and 203b extend out from the sampling portion 201 width of around 2.34 mm on each side. The interface portion 207 width is around 3.81 mm. The sampling portion 201 length is around 15.07 mm. The slits 209 are around 2 mm long and spaced around 2 mm apart at the end (opposite the interface portion 207) and slits 209 along the side of the direct sample collection pad 200 are spaced around 2.5 mm apart and around 2 mm long. The thickness T2 in FIG. 4 is substantially similar to that of thickness T1 (see FIG. 1), however, because slits 209 are included in the direct sample collection pad 200, thickness T2 can be greater than thickness T1.

Figure 5:
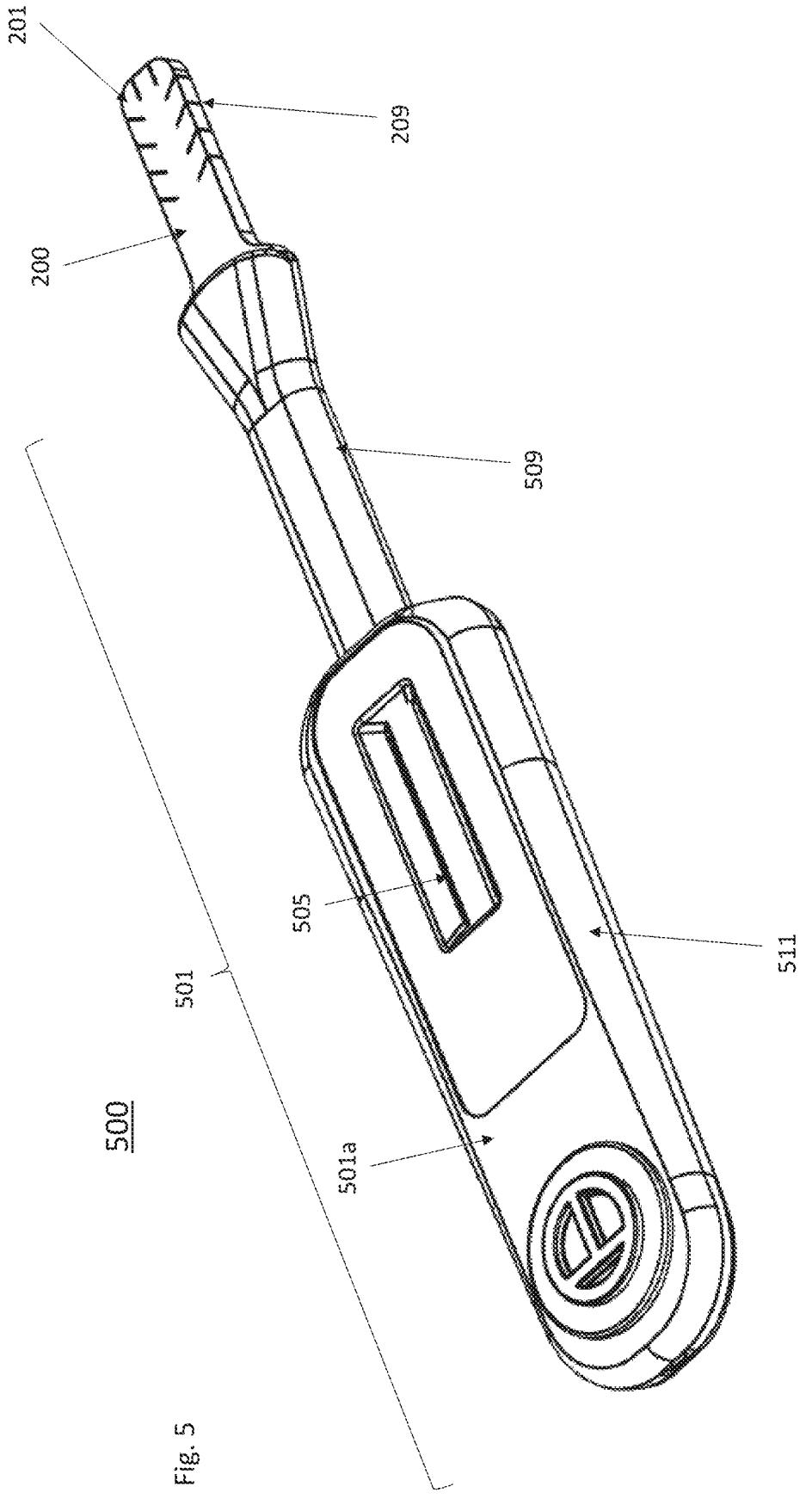
FIG. 5 is an exemplary front perspective view of an assay assembly including the direct sample collection pad in a housing with an assay assembly in accordance with one embodiment of the invention.
Figure 6:
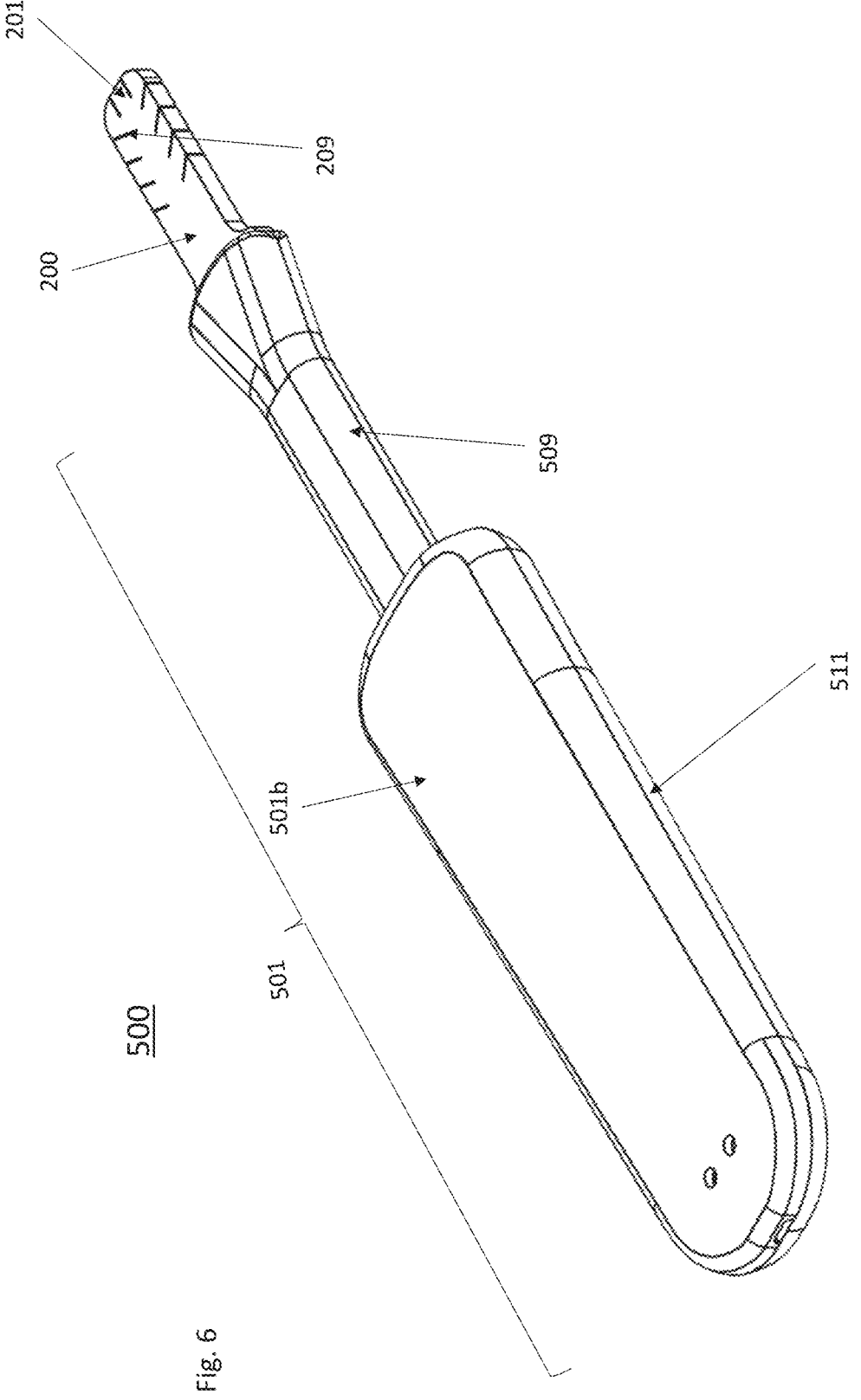
FIG. 6 is an exemplary back perspective view of the assay assembly, of one embodiment of the invention.
Figure 7:
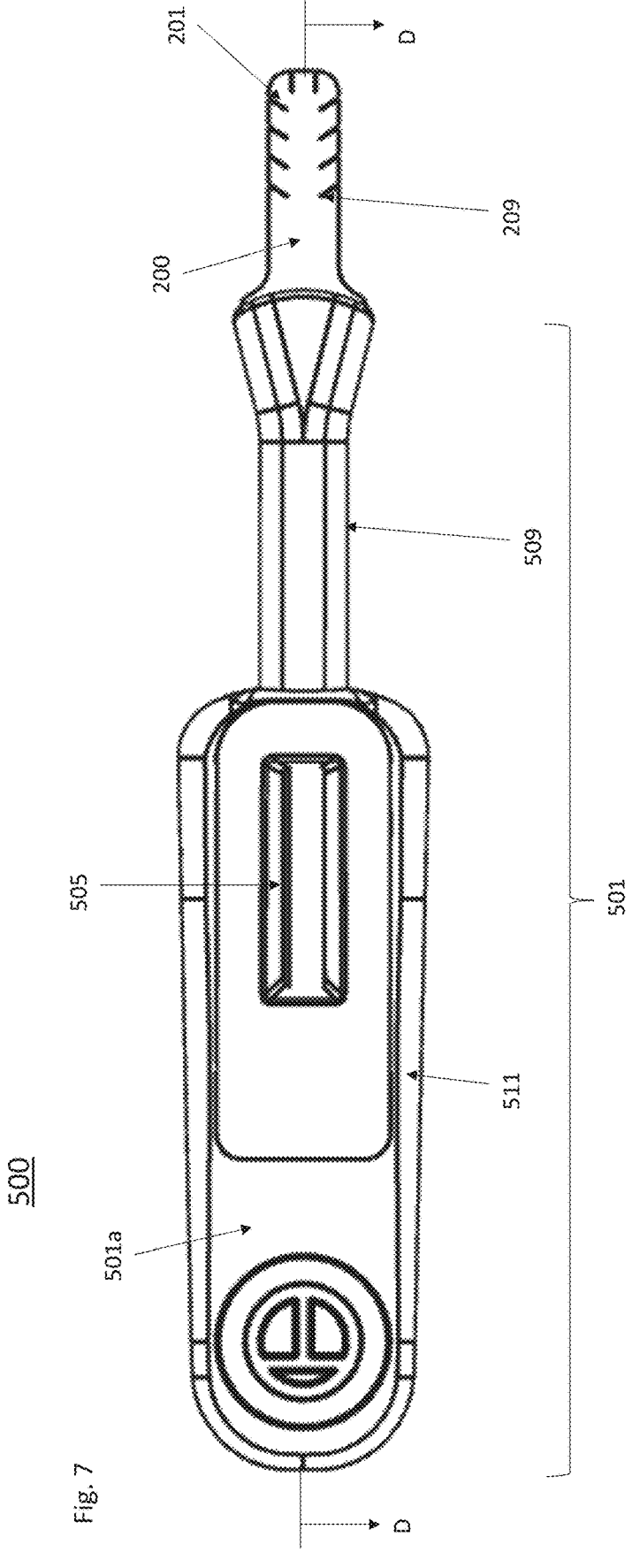
FIG. 7 is an exemplary front view of the assay assembly in accordance with one embodiment of the invention.
Figure 8:
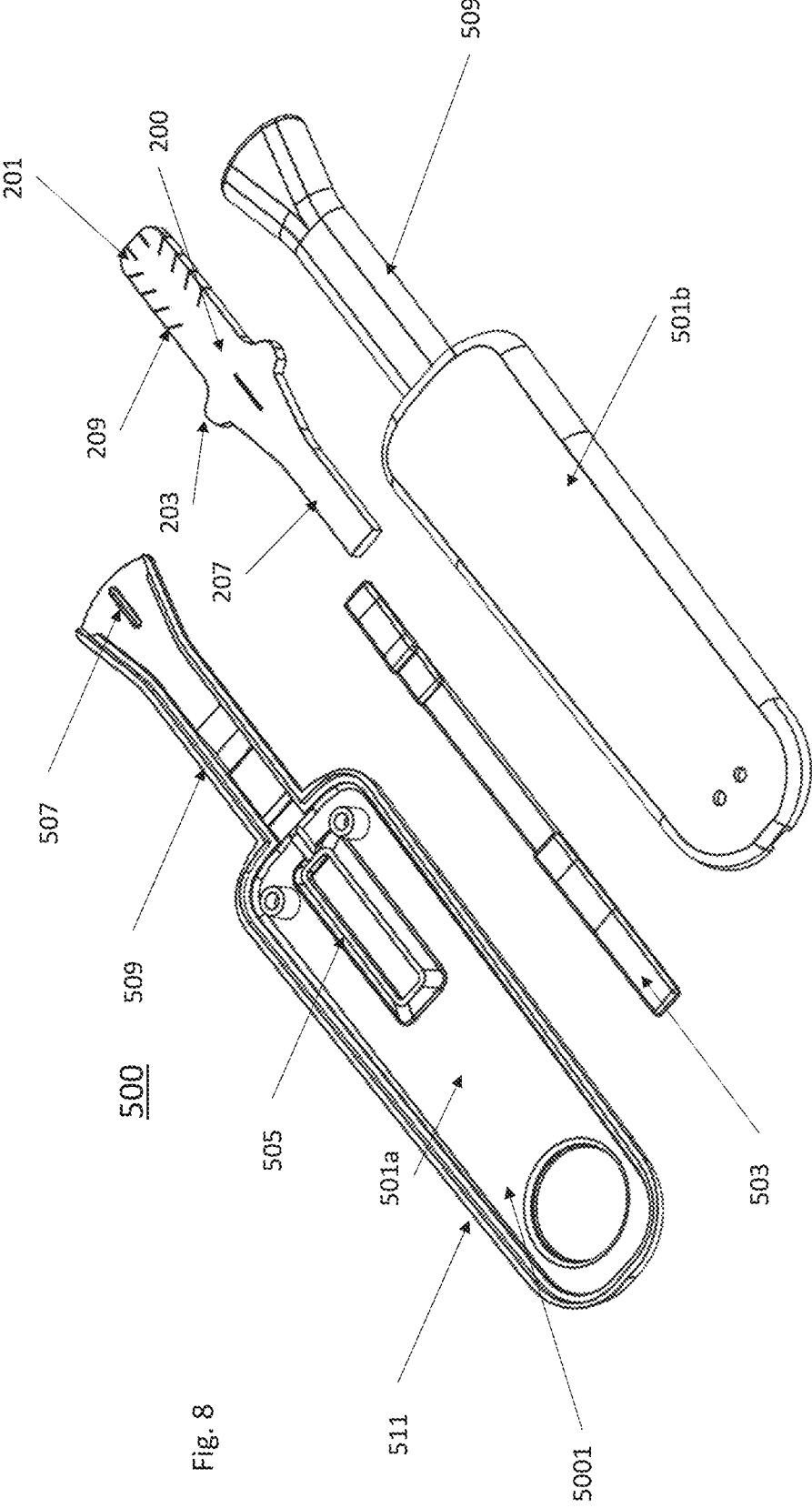
FIG. 8 is an exemplary exploded front perspective view of the assay assembly in accordance with one embodiment of the invention.

FIGS. 5-7 show an exemplary front perspective view, rear perspective view, and front view of the assay assembly 500. The assay assembly 500 includes both the collection pad 200, and housing 501. The housing 501 includes front cover 501a (shown in FIGS. 5 and 7) and rear cover 501b (shown in FIG. 6). The direct sample collection pad 200 is placed between the two halves of the housing 501a and 501b, as seen in FIG. 8. The front cover 501a and rear cover 501b may be held together with any known methods, including with adhesives, fasteners, tabs, ultrasonic welding, etc.

The front view of the housing 501 shown in FIG. 5 includes the front cover 501a of the housing, a base 511, a neck 509, and an indication window 505. The base 511 includes the indication window 505 and is shaped to easily be held by a user. The base 511 includes a substantially rectangular prism with rounded edges. However, in other embodiments can take the shape of a grooved handle or other easily manipulable shape that can control the sampling portion 201 of the collection pad 200.

In some embodiments, the housing 501 can include more than two parts, as long as the housing 501 can be held together as a single unit when in use. The housing 501 encapsulates the assay strip 503 (shown in FIG. 8), which prevents contamination of the assay strip 503. Generally, the assay assembly can be pre-packaged to prevent contamination during transport and before use. The only part of the assay assembly 500 that is temporarily open to the environment is the collection pad 200, which is retained and supported by the housing 501 by at least the interface portion 207 (shown in FIG. 3) and held in place within the housing security portion 205 (shown in FIG. 3).

The neck 509 extends from a base 511 of the housing 501 to the seated wing portion 203. The neck 509 provides a hollow indentation within the housing 501 for surrounding the assay strip 503, the interface portion 207, and seated wing portion 203 of the collection pad 200. In some embodiments, the neck 509 extends beyond the extended portion of the seated wing portion 203 to retain and envelope the seated wing portion 203 from compression when placed in a developer solution vial. In other words, that part of the housing 501 may correspond with an edge of the developer solution vial.

The indication window 505 provides viewable access to the assay strip 503 (as shown in FIG. 8). The indication window 505 may be a clear or an opaque material, which can be used to identify the results of the assay diagnosis.

FIG. 8 shows an exemplary exploded front perspective view of the assay assembly 500. The exploded view shows the assay strip 503 and collection pad 200 as separate components of the assay assembly 500. However, in some embodiments, the assay strip 503 and collection pad 200 can also be a single component.

Figure 9:
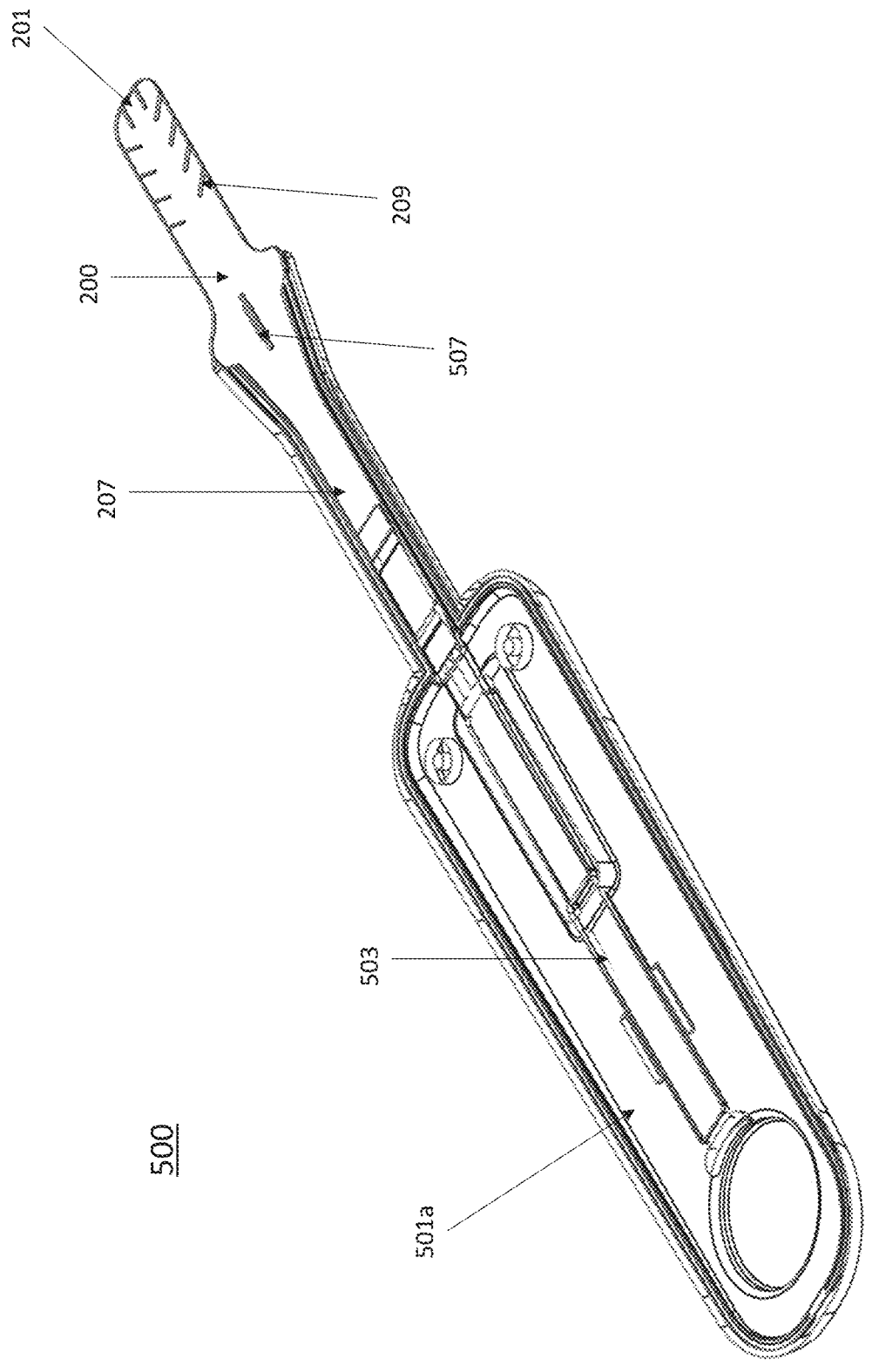
FIG. 9 is an exemplary front perspective view of the direct sample collection pad in a back cover housing of an assay assembly in accordance with one embodiment of the invention.
Figure 10:
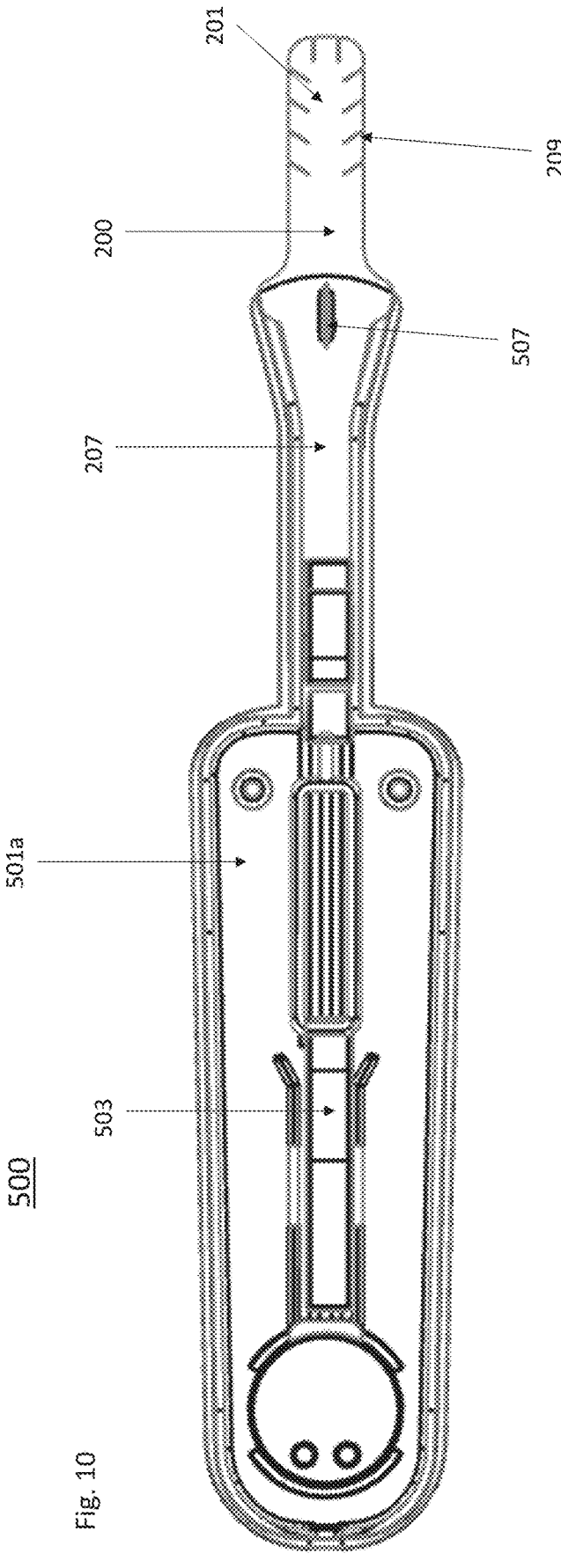
FIG. 10 is an exemplary front view of the direct sample collection pad in a front cover housing of an assay assembly in accordance with one embodiment of the invention.

FIGS. 9 and 10 show an exemplary front perspective view and front view, respectively, of the assay assembly 500 with the assay strip 503 and collection pad 200 placed within the housing 501. The interface portion 207 of the collection pad 200 touches the blocker pad of the assay strip 503, which is enough to allow a sample collected on the sampling portion 201 of the collection pad 200 to be wicked into the assay strip 503 to be tested.

Figure 11:
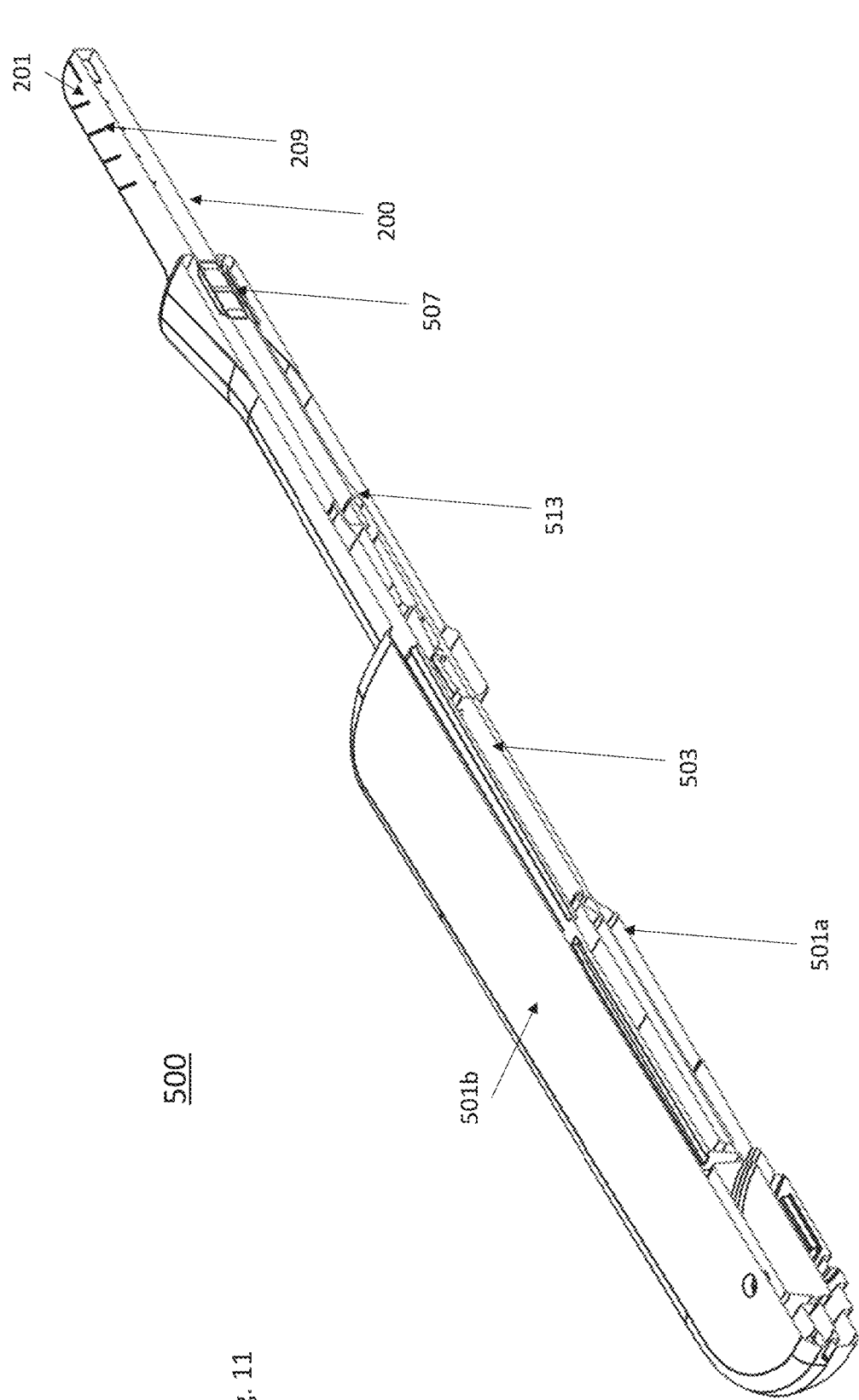
FIG. 11 is an exemplary front perspective view of the direct sample collection pad in a cover housing of an assay assembly in accordance with the invention of FIG. 7 from section D-D.

FIG. 11 shows an exemplary front perspective view of the assay assembly 500 of the invention of FIG. 7 from section D-D. As shown, the protrusion 507 within the housing 501 extends from front cover 501a. In some embodiments, the protrusion can extend from back cover 501b or both covers 501a and 501b to provide a securing extension for the collection pad 200. The cross-sectional view also shows the contact area 513, which is the corresponding surface area (i.e. touching surface area) of the blocker pad of the assay strip 503 and the interface portion 207 of the collection pad 200.

Figures 12A, 12B, 12C:
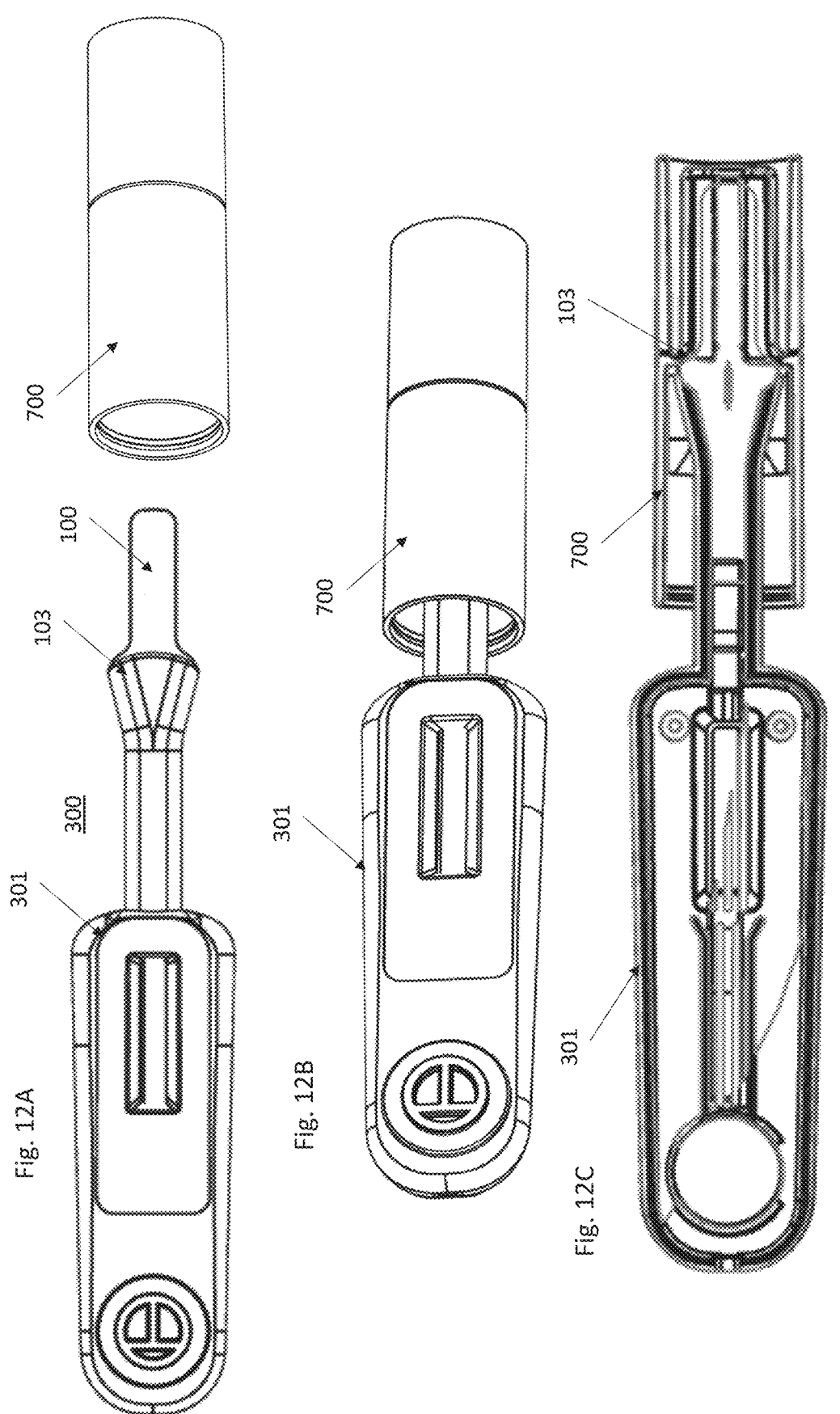
FIGS. 12A-C are exemplary front views of an assay assembly with a direct sample collection pad without slits in use with a developer solution vial in accordance with one embodiment of the invention.

FIGS. 12A-C show exemplary front views of an assay assembly with a direct sample collection pad (without slits) in use with a developer solution vial. The figures show an assay assembly 300 with an integrated direct sample collection pad 100 entering and interfacing with the developer solution vial 700. FIG. 12A shows the assay assembly 300 and developer solution vial 700 separately. FIGS. 12B and 12C show the assay assembly 300 in the developer solution vial 700 from various views, with the base 301 extending out of the vial 700. FIG. 12C shows a cross-sectional view of the mated assay assembly 300 and developer solution vial 700, showing how the assay assembly 300 would be centered and rests at seated wing portions 103 on a corresponding contoured interior surface of the vial 700.

Figures 13A, 13B, 13C:
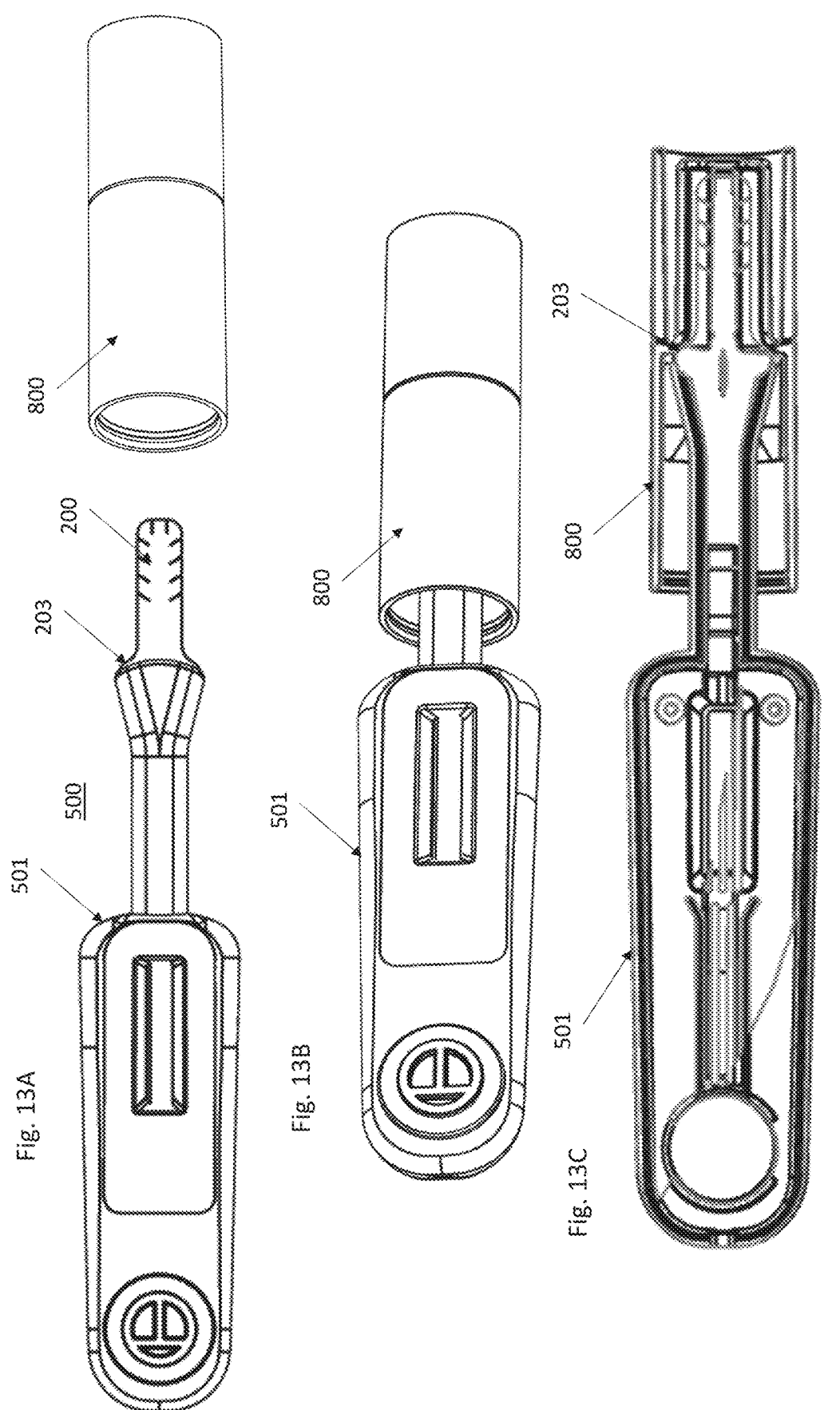
FIGS. 13A-C are exemplary front views of an assay assembly with a direct sample collection pad with slits in use with a developer solution vial in accordance with one embodiment of the invention.

FIGS. 13A-C show exemplary front views of an assay assembly with a direct sample collection pad (with slits) in use with a developer solution vial. The figures show an assay assembly 500 with an integrated direct sample collection pad 200 entering interfacing with the developer solution vial 800. FIG. 13A shows the assay assembly 500 and developer solution vial 800 separately. FIGS. 13B and 13C show the assay assembly 500 in the developer solution vial 800 from various views. FIG. 13C shows a cross-sectional view of the mated assay assembly 500 and developer solution vial 800, showing how the assay assembly would be centered and rests at seated wing portions 203 on a corresponding contoured interior surface of the vial 800.

Figures 14A, 14B, 14C:
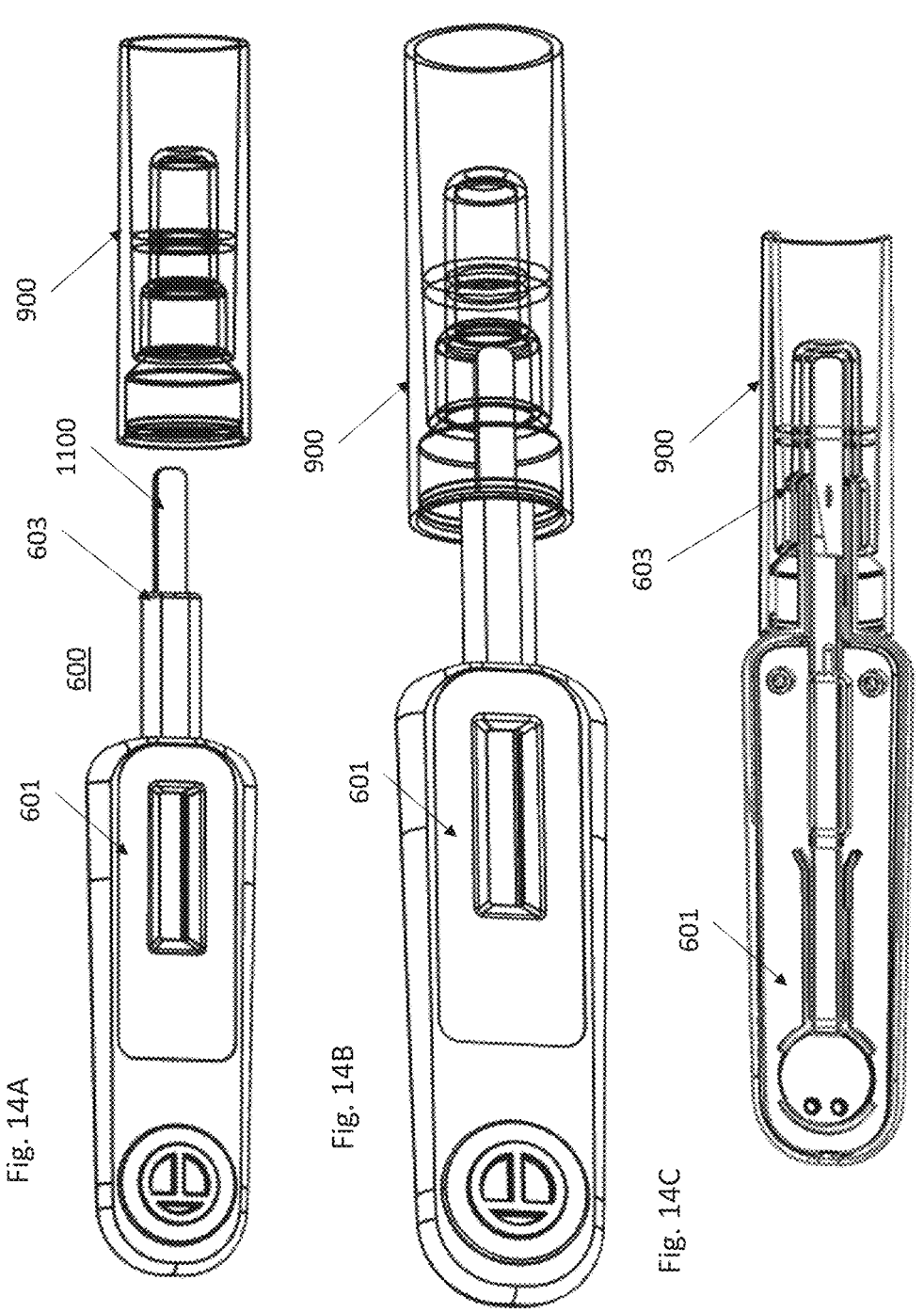
FIGS. 14A-C are exemplary front view of another assay assembly in use with another developer solution vial in accordance with one embodiment of the invention.

FIGS. 14A-C show exemplary front views of another embodiment of the invention with an assay assembly in use with another developer solution vial. The figures show an assay assembly 600 entering and interfacing with the developer solution vial 900. FIG. 14A shows the assay assembly 600 and developer solution 900 separately. FIGS. 14B and 14C shows the assay assembly 600 in the developer solution vial 900 from various views, with the base 601 extending out of the vial 900. FIG. 14C shows a cross-sectional view of the assay assembly 600 and another developer solution vial 900, showing how the assay assembly 600 is centered and resting at a seating portion 603 of the assay assembly housing on a corresponding contoured interior surface of the vial 900. The assay assembly 600 includes a direct sample collection pad without a seated wing portion, and thus the seating portion 603 is part of the housing of the assay assembly 600.

Sampling and Testing

In one exemplary embodiment, an assay method comprises the steps of collecting a sample on a direct sample collection pad integrated with an assay assembly. The direct sample collection pad is placed in contact with a surface or a bodily fluid and manipulated (e.g., pressed and dragged along a surface or swirled in a bodily fluid) to collect a sample for a valid diagnosis. The direct sample collection pad of the assay assembly with the collected sample is inserted into a developer solution vial to submerge the direct sample collection pad of the assay assembly in the developer solution within the cavity of the developer solution vial to wet the direct sample collection pad with the developer solution and to run the assay for the diagnosis.

In one embodiment, a method for using a developer solution vial with an assay assembly to diagnose a respiratory disease in a patient is performed. The method can be broken down into two main steps. The first step is collection, and the second step is testing.

In one embodiment, the collection step begins with bringing the tests including both the developer solution vial and LFA to an operating temperature of 15°-40° C. (59°-104° F.). A testing stand is placed to receive a resting developer solution vial. Another embodiment of the invention is a kit (not shown) where the LFA and developer solution vial come in a dual-chamber pouch, which keeps the developer solution vial and LFA sanitary and prevents accidental adulteration of a test. The developer solution vial includes a cap, which is gently rocked off the developer solution vial and seals the developer solution in the developer solution vial prior to use. The developer solution vial is placed into the slot in the stand.

The patient may then be instructed to blow their nose into a tissue and then discard. The patient removes the LFA device, such as assay assembly 500 above, from the pouch and checks for an absorbent packet, which prevents absorption of liquid by the collection pad of an LFA. The collection pad should not be touched. The collection pad from the assay assembly is pressed firmly into a nostril against the nasal wall and rotated a number of times (15) in each nostril.

The testing step begins by inserting the assay assembly into the developer solution vial on the testing stand. See FIGS. 13A-13C. In one embodiment, the developer solution vial 800 uses an assay assembly 500 that is configured to allow direct sample collection with an assay assembly 500 with an integrated direct sample collection pad 200. Agitation may not be necessary to elute the sample from the direct sample collection pad 200. Rather, simply inserting the assay assembly into the developer solution vial 800 may wick the sample directly into the through the assay strip of the assay assembly 500.

The user should make sure to leave a results window of the assay assembly facing the user. The user then leaves the assay assembly in the developer solution vial for between 30 and 40 minutes while the test is running. In one embodiment, a pink indicator fluid will appear and be wicked to the results window.

In some embodiments, the developer solution vial 800 may be shipped separate from the developer solution. Thus, the developer solution vial 800 may require filling. In some embodiments, the developer solution vial 800 may be made of a translucent, opaque, or transparent material that allows a user to see a mark for a fill-line and/or the amount of developer solution that has been added to the developer solution vial 800.

In some embodiments, the assay assembly may be agitated in the developer solution by swirling the collection pad of the assay assembly a number of times (10) and then leaving the assay assembly in the developer solution and returned to the testing stand. In other embodiments, the assay assembly may be spun, tapped, or plunged up and down in the developer solution to elute the sample from the assay assembly with the integrated direct sample collection pad, and into the developer solution.

In some embodiments, the direct sample collection pad 100 or 200 may be wet with developer solution before collection of the sample from the patient.

The sample may be collected from a patient or surface by pressing, swabbing, wiping, or dabbing at a bodily fluid of the patient or the surface. The collecting may require the user to wipe a surface or bodily fluid a number of times to better ensure collection of enough sample for the assay strip to run the diagnosis. For example, wiping at the anterior nares five times to ensure good coverage by the assay assembly.

Once the sample is collected, then the assay assembly is inserted into the developer solution vial in the developer solution containing the sample to run the assay for diagnosis. The assay assembly may include any fluid flow assay assemblies, however, a lateral flow assay device is preferred.

The direct sample collection pad of the assay assembly 500 is then inserted into a developer solution vial 800 to submerge the direct sample collection pad in the developer solution within the cavity of the vial to wet the direct sample collection pad with the solution. Specifically, in the case of an assay assembly integrated with a direct sample collection pad, once a sample is collected on direct sample collection pad of the assay assembly, the direct sample collection pad side of the assay assembly is inserted into the developer solution vial. The developer solution vial cavity is filled with the developer solution and inserting the direct sample collection pad into the developer solution vial wets the direct sample collection pad and wicks the sample into the rest of the assay assembly. The sample moves through the assay strip of the assay assembly and eventually displays the results for diagnosis.

Optionally, the sample may be removed from the direct sample collection pad by elution in order to wick the sample through the assay strip. The elution may be through any number of methods from agitating the direct sample collection pad in the developer solution to pressing the direct sample collection pad against a side of the developer solution vial to forcefully remove the sample from the direct sample collection pad. Elution may also be through agitating the direct sample collection pad at a depth within the developer solution to submerge the head of the direct sample collection pad and mixing the sample with the developer solution may include swirling, rotating, shaking, tapping, push-pull motion, etc. The agitation should limit or prevent spillage of developer solution.

Although the invention has been described with reference to various exemplary embodiments, it is to be understood that these embodiments are merely illustrative of the principles and applications of the invention. Those having skill in the art would recognize that various modifications to the exemplary embodiments may be made, without departing from the scope of the invention. Various features and/or characteristics of differing embodiments of the invention may be combined with one another. Any directional aspects of a direct sample collection pad and assay assembly of the invention as it is described, oriented or appears in the drawings are presented for convenience only; they are not intended to be limiting or to imply that the device must be used or positioned in any particular orientation.

The claimed invention is:

1. An assay assembly and a developer solution vial combination for diagnosing patients, comprising:
   the developer solution vial, the developer solution vial comprising a seating surface and a cavity, the cavity having a bottom surface and containing a developer solution; and
   the assay assembly, the assay assembly comprising:
   a housing;
   an assay strip; and
   an elongated direct sample collection pad partially received inside and extending beyond the housing to terminate at a distal end, the elongated direct sample collection pad comprising:
      a sampling portion with slits to provide flexibility to the elongated direct sample collection pad,
      a seating portion to provide a contoured surface to rest on the seating surface of the developer solution vial while positioning the distal end of the elongated direct sample collection pad in spaced relation from the bottom surface of the cavity of the developer solution vial when the elongated direct sample collection pad is placed in the developer solution vial to prevent direct contact between the distal end and the bottom surface of the cavity of the developer solution vial, wherein the seating portion comprises first and second seated wing portions extending beyond an outer edge of an opening of the cavity of the developer solution vial when the elongated direct sample collection pad is placed in the developer solution vial, and
      an interfacing portion overlapping a portion of the assay strip.

2. The assay assembly and developer solution vial combination of claim 1, wherein the slits are evenly spaced along an edge of an end of the sampling portion.

3. The assay assembly and developer solution vial combination of claim 1, wherein the slits are cut directionally toward a longitudinal center line and an opposite end of the elongated direct sample collection pad.

4. The assay assembly and developer solution vial combination of claim 1, wherein the elongated direct sample collection pad has a thickness that provides a rigidity that limits deformation of the elongated direct sample collection pad when sampling from a surface.

5. The assay assembly and developer solution vial combination of claim 1, wherein the sampling portion includes a size and shape for minimizing a void volume of the developer solution vial when the elongated direct sample collection pad is placed in the developer solution vial.

6. An assay assembly and a developer solution vial combination for diagnosing patients, comprising:
   the developer solution vial, the developer solution vial comprising a seating surface and a cavity, the cavity having a bottom surface and containing a developer solution; and
   the assay assembly, the assay assembly comprising:
   a housing;
   an assay strip; and
   an elongated direct sample collection pad partially received inside and extending beyond the housing to terminate at a distal end, the elongated direct sample collection pad comprising:
      a sampling portion with slits to provide flexibility to the elongated direct sample collection pad,
      a seating portion to provide a contoured surface to rest on the seating surface of the developer solution vial while positioning the distal end of the elongated direct sample collection pad in spaced relation from the bottom surface of the cavity of the developer solution vial when the elongated direct sample collection pad is placed in the developer solution vial to prevent direct contact between the distal end and the bottom surface of the cavity of the developer solution vial, wherein the seating portion comprises first and second seated wing portions extending beyond an outer edge of an opening of the cavity of the developer solution vial when the elongated direct sample collection pad is placed in the developer solution vial,
      a securing portion to prevent the elongated direct sample collection pad from moving when the elongated direct sample collection pad is placed in the housing, and
      an interfacing portion overlapping a portion of the assay strip.

7. The assay assembly and developer solution vial combination of claim 6, wherein the slits are evenly spaced along an edge of an end of the sampling portion.

8. The assay assembly and developer solution vial combination of claim 6, wherein the slits are cut directionally toward a longitudinal center line and an opposite end of the elongated direct sample collection pad.

9. The assay assembly and developer solution vial combination of claim 6, wherein the elongated direct sample collection pad has a rigidity that limits deformation of the elongated direct sample collection pad when sampling from a surface.

10. The assay assembly and developer solution vial combination of claim 6, wherein the sampling portion includes a size and shape for minimizing a void volume of the developer solution vial when the elongated direct sample collection pad is placed in the developer solution vial.

11. The assay assembly and developer solution vial combination of claim 1, wherein the sampling portion of the elongated direct sample collection pad is made of a wicking material.

12. The assay assembly and developer solution vial combination of claim 11, wherein the wicking material is a nitrocellulose material.

13. The assay assembly and developer solution vial combination of claim 6, wherein the sampling portion of the elongated direct sample collection pad is made of a wicking material.

14. The assay assembly and developer solution vial combination of claim 13, wherein the wicking material is a nitrocellulose material.

15. The assay assembly and developer solution vial combination of claim 1, wherein the first and second seated wing portions have rounded smooth edges proximate to the sampling portion and configured to rest on the opening of the cavity of the developer solution vial when the elongated direct sample collection pad is placed in the developer solution vial.

16. The assay assembly and developer solution vial combination of claim 15, wherein the first and second seated wing portions are symmetrical.

17. The assay assembly and developer solution vial combination of claim 6, wherein the first and second seated wing portions have rounded smooth edges proximate to the sampling portion and configured to rest on the opening of the cavity of the developer solution vial when the elongated direct sample collection pad is placed in the developer solution vial.

18. The assay assembly and developer solution vial combination of claim 17, wherein the first and second seated wing portions are symmetrical.

* * * * *